United States Patent
Lesiv et al.

(10) Patent No.: US 12,383,523 B2
(45) Date of Patent: Aug. 12, 2025

(54) MAGNETIC RESONANCE IMAGING DRUG CONTAINING DEUTERATED SARCOSINE, AND DIAGNOSTIC METHOD USING SAID DRUG

(71) Applicant: LIMITED LIABILITY COMPANY "SOLVEX" ("SOLVEX" LLC), Moscow (RU)

(72) Inventors: Aleksei Valerevich Lesiv, Moskovskaya obl. (RU); Pavel Evgenevich Ivashkin, Moscow (RU); Aleksei Viktorovich Kosenkov, Moscow (RU); Vladimir Ivanovich Polshakov, Moscow (RU); Mikhail Valentinovich Kisilevskii, Moscow (RU)

(73) Assignee: LIMITED LIABILITY COMPANY "SOLVEX", Moscow (RU)

( * ) Notice: Subject to any disclaimer, the term of this patent is extended or adjusted under 35 U.S.C. 154(b) by 977 days.

(21) Appl. No.: 17/419,638

(22) PCT Filed: May 8, 2019

(86) PCT No.: PCT/RU2019/000325
§ 371 (c)(1),
(2) Date: Jun. 29, 2021

(87) PCT Pub. No.: WO2020/139127
PCT Pub. Date: Jul. 2, 2020

(65) Prior Publication Data
US 2022/0079905 A1    Mar. 17, 2022

(30) Foreign Application Priority Data
Dec. 29, 2018  (RU) ................................ 2018147613

(51) Int. Cl.
| | | |
|---|---|---|
| *A61K 31/19* | (2006.01) | |
| *A61B 5/055* | (2006.01) | |
| *A61K 31/198* | (2006.01) | |
| *A61K 49/10* | (2006.01) | |

(52) U.S. Cl.
CPC ............ *A61K 31/198* (2013.01); *A61B 5/055* (2013.01); *A61K 49/10* (2013.01)

(58) Field of Classification Search
CPC .................................................... A61K 31/198
See application file for complete search history.

(56) References Cited

U.S. PATENT DOCUMENTS

2018/0284075 A1*  10/2018  Ojima .................... G01N 1/405

FOREIGN PATENT DOCUMENTS

RU          2 663 286       8/2018

OTHER PUBLICATIONS

Wu, et al. Anal. Bioanal. Chem. (2011) 401:635-646.*
Registry No. 1219794-62-3 and Registry No. 347840-04-4. Retrieved from STN; entered in STN on Apr. 21, 2010.*
International Search Report for PCT/RU2019/000325 dated Oct. 3, 2019, 3 pages.
Written Opinion of the ISA for PCT/RU2019/000325 dated Oct. 3, 2019, 4 pages.
A. Cohen et al., "Synthesis of 2-Amino-1, 5-Dihydro-1-(Methyl-13C)-4H-Imidazol-4-One-5-13C (Creatinine-13C2)," Journal of Labelled Compounds and Radiopharmaceuticals, Jun. 1986, vol. 24, No. 5, pp. 587-597.
Pascal A. T. Baltzer et al., "False-Positive Findings at Contrast-Enhanced Breast MRI: A BI-RADS Descriptor Study," American Journal of Roentgenology, Jun. 2010, vol. 194, No. 6, pp. 1658-1663.
Robert E. London, "In Vivo $^2$H NMR Studies of Cellular Metabolism," Biological Magnetic Resonance, In Vivo Spectroscopy, vol. 11, Berliner L.J., Reuben, J. (Eds.), Springer, 1992, pp. 278-283.
F.H. Glorieux et al., "Transport and Metabolism of Sarcosine in Hypersarcosinemic and Normal Phenoypes," The Journal of Clinical Investigation, 1971, vol. 50, pp. 2313-2322.
R.M. Johnstone et al., "Amino Acid Transport in Tumor Cells," Advances in Cancer Research, 1965, vol. 9, pp. 143-226.
R.H. Abeles et al., "A Dual Isotope Effect in the Enzymatic Oxidation of Deuteromethyl Sarcosine," The Journal of Biological Chemistry, Mar. 1960, vol. 235, No. 3, pp. 853-856.
S. De Vogel et al., "Sarcosine and other Metabolites Along the Choline Oxidation Pathway in Relation to Prostate Cancer—A Large Nested Case-Control Study Within the JANUS Cohort in Norway," International Journal of Cancer, Jan. 2014, 134, 1, pp. 197-206.
H. Shahid et al., "An Overview of Breast MRI," Applied Radiology, Oct. 2016, 45, pp. 7-13.
C. Taglang et al., "Late-Stage Deuteration of 13C-Enriched Substrates for T1 Prolongation in Hyperpolarized 13C MRI," Chem Comm, May 2018, pp. 5233-5236.
H. Gries, "Topics in Current Chemistry," Extracellular MRI Contrast Agents Based on Gadolinium, Contrast Agents I—Magnetic Resonance Imaging, Krause, W. (Ed.), Springer, 2002, pp. 1-24.
V. Kepe et al., "Position Emission Tomography of Sodium Glucose Cotransport Activity in High Grade Astrocytomas," Journal of Neuro-Oncology, Mar. 2018, 138, 5, pp. 557-569.
W.R. Frisell et al., "The Binding Sites of Sarcosine Oxidase," J. Biol. Chem. Nov. 1955, 217, 1, pp. 275-285.

(Continued)

Primary Examiner — Shawquia Jackson
(74) Attorney, Agent, or Firm — Nixon & Vanderhye PC

(57) ABSTRACT

The invention relates to the means for magnetic resonance imaging of oncological diseases and other diseases, accompanied by a locally altered level of absorption of nutrients by cells. The invention is the diagnostic drug containing at least one deuterated derivative of sarcosine, as well as the diagnostic method based on the use of this diagnostic drug. The method of the invention includes performing magnetic resonance imaging and/or deuterium magnetic resonance spectroscopy after administration of the diagnostic drug in a time sufficient for the accumulation of the diagnostic drug in a target area of a subject's body. The proposed method allows to carry out a highly informative diagnostics of oncological diseases and other diseases, accompanied by a locally altered level of absorption of nutrients by cells.

18 Claims, 3 Drawing Sheets

(56) References Cited

OTHER PUBLICATIONS

Mauger A.B. et al.Two distinct site-dependent biosynthetic pathways for the incorporation of sarcosine into actinomycins; Archives of Biochemistry and Biophysics, vol. 176, Issue 1, Sep. 1976, pp. 181-186.

Soliman Laiel C. et al. Monitoring potential prostate cancer biomarkers in urine by capillary electrophoresis-tandem mass spectrometry; Journal of Chromatography A, p. 162-169, Jul. 14, 2012.

Allen R.H. et al. Serum betaine, N,N-dimethylglycine and N-methylglycine levels in patients with cobalamin and folate deficiency and related inborn errors of metabolism; Metabolism Nov. 1993; 42(11):1448-60.

Mei Chen Sarcosine a novel marker of prostate cancer and exploration of diagnostic threshold Range; Science and Technology Series of Medicine Section of China Excellence in Master Engineering Papers Database, p. E072-601, Apr. 15, 2018.

* cited by examiner a) sarcosine-4,4,4-d₃ b) sarcosine-2,2,4,4,4-d₅ b) mixture of sarcosine-2,2-d₂ and sarcosine-4,4,4-d₃ a b a) alanine-$d_3$ b) phenylalanine-$d_7$

MAGNETIC RESONANCE IMAGING DRUG CONTAINING DEUTERATED SARCOSINE, AND DIAGNOSTIC METHOD USING SAID DRUG

This application is the U.S. national phase of International Application No. PCT/RU2019/000325 filed May 8, 2019 which designated the U.S. and claims priority to RU patent application No. 2018147613 filed Dec. 29, 2018, the entire contents of each of which are hereby incorporated by reference.

TECHNICAL FIELD

The invention relates to medicine, namely to the means for magnetic resonance imaging.

PRIOR ART

Non-invasive diagnostics of diseases, including early diagnostics, is a key priority area in healthcare. One of the informative methods for the diagnostics of diseases is magnetic resonance imaging (MRI).

Most types of MRI used in clinical practice are based on recording the magnetic resonance signal of protons ($^1$H nuclei) contained in a human body water. $^1$H MRI provides a high degree of anatomical detailing. At the same time, it is known from the clinical practice that MRI does not always provide unambiguous data about the nature of a disease. In particular, in oncology, a reliable distinction between malignant tumors and non-life-threatening benign formations, foci of inflammation, etc. remains challenging [see, for example: Baltzer, P.A.T. et al. Am. J. Roentenology, 2010, 194, 1658-1663; Shahid, H. et al. Appl. Radiol. 2016, 45, 7-13.]. In this regard, early diagnosis of oncological diseases is also difficult, since the risk of a false-positive result is high.

The main method to make $^1$H MRI more informative is to use contrast agents that change the relaxation time of water protons in their environment [Topics in Current Chemistry, Contrast Agents I, Magnetic Resonance Imaging. Krause, W. (Ed.), Springer, 2002]. A wide range of contrast agents are known for being used in MRI diagnostics, including the commercially available Omniscan®, Magnevist®, ProHance® and Clariscan®, which are gadolinium complexes, as well as Feridex® and Resovist®, which are aqueous suspensions of stabilized magnetic nanoparticles. In addition to enhancing the contrast of images, these substances allow the assessment of perfusion.

An alternative to $^1$H MRI with contrast agents is a registration of the signal from other nuclei, in particular, methods using isotopes $^{31}$P, $^{13}$C, $^{19}$F, $^{23}$Na are at different stages of their clinical trials.

Deuterium ($^2$H) is a natural, non-radioactive isotope of hydrogen, the content of which in biological objects is 0.0156% of the total amount of hydrogen.

Document U.S. Pat. No. 5,042,488 showed the possibility of registering the deuterium signal after injection of $D_2O$ and 1-deuteroglucose in vivo (in rat's liver).

Document US20030211036 A1 proposed a method for measuring perfusion in selected tissue sections using isotopically labeled compounds (e.g. $D_2O$) by analogy with paramagnetic contrast agents.

Document US20100322865 A1 describes the use of metabolic water precursors to estimate metabolic rate. 1,2,3,4,5 6,6-deuterated glucose is mentioned as an example of a metabolic precursor of HOD. Within the framework of the described invention, only NMR signals on metabolic water deuterium and aliphatic chain of fatty acids are recorded, and there are no NMR signals of deuterated glucose.

Despite the widespread clinical application of $^1$H MRI technology, there remains a need for developing new, more effective methods of MRI diagnostics.

DISCLOSURE OF THE INVENTION

The goal of this invention is to develop a new effective diagnostic drug for diagnosing diseases by means of MRI and/or MR spectroscopy and a diagnostic method involving the use of the specified drug.

The technical result of this invention is to create a new and effective diagnostic drug that can be used for non-invasive diagnosis of diseases and pathological processes accompanied by a locally altered (increased or decreased) level of nutrients absorption by cells, in particular, oncological diseases, by means of magnetic resonance imaging and/or deuterium magnetic resonance spectroscopy.

This technical result is achieved through the development of the diagnostic drug that is compatible with the fundamental physical limitations of the nuclear magnetic resonance method (MRI or MR spectroscopy). It is known that the gyromagnetic ratio of the deuterium nucleus is 6.5 times less than that of protium. As a consequence, the detection sensitivity of the deuterium signal is approximately 0.01 (i.e. 1%) of the detection sensitivity of the protium signal [Biological Magnetic Resonance, Volume 11, In Vivo Spectroscopy. Berliner L.J., Reuben, J. (Eds.), Springer, 1992]. A weak signal can be recorded by averaging the signal of several identical scans. However, such averaging requires an increase in the scan time, and the signal-to-noise ratio increases non-linearly (proportionally,$\sqrt{n}$ where n is the number of scans; for example, if the scan takes 10 minutes, and the signal-to-noise ratio should be increased by 10 times, an increase in the scan time will be required by 100 times, i.e. up to 16 hours). At that, the duration of scanning in living organisms is limited by both pharmacokinetics of the diagnostic drug and practical applicability in clinical practice (the examination should not take more than 1-2 hours) and the need for a patient to stay immobile during the entire scanning period. The intensity of the magnetic resonance signal also depends on the strength of the magnetic field. Since MR tomographs with a magnetic field strength of no more than 7T are currently approved for clinical application, only those diagnostic drugs that provide a sufficient signal intensity at 7T are practically applicable.

Thus, the deuterated compound in the diagnostic drug of the invention should have such a set of physicochemical and biological properties that ensures both the selective accumulation of deuterium and the maintenance of its concentration in the target tissues for a time sufficient for signal recording. The lower the concentration of the deuterated compound achieved in the tissue, the longer it is required to average the signal and, therefore, the longer the deuterated compound is to be in the tissues, maintaining a selective distribution. On the other hand, increasing the dose of the diagnostic drug is not a universal solution, since its excretion can be accelerated (in particular, by exceeding the reabsorption capacity of the kidneys), the risk of toxicity increases, the selectivity of accumulation in various tissues decreases, moreover the dose is limited by solubility.

For the most chemical compounds, including amino acids, there are no data on the maximum achievable non-toxic concentrations in tissues in case of pathology. As a consequence, the development of the diagnostic drug that meets the above criteria requires experimental evidence of its applicability in $^2$H MRI and/or in vivo MR spectroscopy.

The technical result of the present invention is also the development of a new effective and informative method for diagnosing diseases and pathological processes accompanied by a locally altered (increased or decreased) level of nutrients absorption by cells, in particular, oncological diseases, by means of magnetic resonance imaging and/or deuterium magnetic resonance spectroscopy including the introduction of the diagnostic drug of the invention, which is capable of accumulating in the target tissues and organs (in particular, in the tumor tissue) in a concentration sufficient to register an informative deuterium tomogram or $^2$H-NMR spectrum in vivo. Additional technical results in the implementation of the invention are the ability to obtain information about the level of perfusion at different points of the scanned region, information about the structure of a tumor, its boundaries, about the malignancy or benignity of the tumor. Another additional technical result is the possibility of assessing the local rate of metabolic processes in the scanned region, which, in turn, makes it possible to assess the level of a metabolic activity and/or cell proliferation, the rate of tumor growth and is an additional parameter that increases the reliability and validity of the diagnostics.

The method of the invention is also characterized by the fact that it is carried out without the harmful effects of ionizing radiation (typical, for example, for CT, PET, SPECT imaging), which in turn increases the safety of examinations, makes it possible to conduct more frequent repeated examinations, in particular, makes the method attractive for the pediatrics. The invention is aimed at obtaining a diagnostic information similar to the method of positron emission tomography or single-photon emission computed tomography (deviation of the level or rate of drug accumulation in pathological tissue from the norm or from the values achieved in the surrounding parts of the same tissue/the same organ), and yet eliminates the risks associated with ionizing radiation of radiopharmaceuticals. In addition, unlike radiopharmaceuticals for PET, the production of deuterated drugs of the invention is not limited to the synthesis and logistics of small batches of short lived isotopes.

Specified technical results are achieved through the development of the diagnostic drug comprising a deuterated derivative of sarcosine and/or its pharmaceutically acceptable salt or mixture thereof for the diagnosis of diseases by means of magnetic resonance imaging and/or deuterium magnetic resonance spectroscopy.

Thus, the first aspect of the invention is the diagnostic drug comprising at least one compound selected from a deuterated sarcosine derivative and/or a pharmaceutically acceptable salt of a deuterated sarcosine derivative for the diagnosis of diseases or pathological processes by means of magnetic resonance imaging and/or deuterium magnetic resonance spectroscopy.

In some embodiments of the invention, the diagnostic drug additionally comprises at least one pharmaceutically acceptable excipient. In some specific cases, the pharmaceutically acceptable excipient is a carrier, filler and/or diluent.

In some embodiments of the invention, the diagnostic drug additionally comprises a sarcosine metabolism inhibitor and/or a sarcosine membrane transport inhibitor. In some specific cases, a sarcosine membrane transport inhibitor is glycine or proline. An inhibitor of sarcosine metabolism is a pharmaceutically acceptable inhibitor of sarcosine demethylation, in particular acetic acid or a salt thereof.

In some embodiments of the invention, the deuterated sarcosine derivative and/or its pharmaceutically acceptable salt, along with deuterium atoms bonded to carbon atoms, contains deuterium atoms partially or completely replacing mobile hydrogen atoms bonded to oxygen and/or nitrogen atoms.

In some embodiments of the invention, the diagnostic drug comprises a deuterated derivative of sarcosine containing deuterium atoms in both the 2nd and 4th positions, or a pharmaceutically acceptable salt thereof; or a mixture of deuterated derivatives of sarcosine and/or their pharmaceutically acceptable salts, where there is at least one deuterated derivative, which contains deuterium atoms in the 2nd position, and at least one deuterated derivative, which contains deuterium atoms in the 4th position.

In some specific embodiments of the invention, a deuterated sarcosine derivative is sarcosine-4,4,4-$d_3$, sarcosine-2,2-$d_2$, or sarcosine-2,2,4,4,4-$d_5$.

In some other embodiments of the invention, the diagnostic drug comprises a mixture of at least two different compounds selected from a deuterated sarcosine derivative and/or a pharmaceutically acceptable salt of a deuterated sarcosine derivative. In some specific embodiments of the invention, the diagnostic drug comprises a mixture of at least two compounds selected from sarcosine-4,4,4-$d_3$, sarcosine-2,2-$d_2$, and sarcosine-2,2,4,4,4-$d_5$.

Another aspect of the invention is a method for diagnosing a disease or pathological process in a subject, comprising the following steps:

administering a diagnostic drug of the invention to a subject;

conducting magnetic resonance imaging and/or deuterium magnetic resonance spectroscopy after the administration of the diagnostic drug in a time sufficient for its accumulation in a target tissue, to obtain, respectively, a tomogram (deuterium tomogram) and/or NMR spectrum (spectra);

diagnosing the presence or absence of a disease based on the observed deuterium nuclei signal intensity, reflecting the level of accumulation of the diagnostic drug.

In preferred embodiments of the invention, the diagnosed disease or pathological process is accompanied by a locally altered (increased or decreased) level of nutrients absorption by cells.

In some embodiments of the invention, the pathological process is an inflammatory process, an infectious process, a process accompanied by active regeneration, a disease associated with ischemia of organs and tissues, graft rejection reaction, an autoimmune disease. In some other embodiments of the invention, the disease is an oncology disease. In some specific embodiments of the invention, an oncology disease is a solid tumor or tumor metastases, including lymph node metastases.

In some embodiments of the invention, the presence or absence of a disease is diagnosed by comparing the signal intensity of deuterium nuclei in a subject undergoing an examination with the typical signal intensity observed in healthy subjects in a target tissue or organ. In some other embodiments of the invention, the presence or absence of a disease is diagnosed based on a comparison of the signal intensity of deuterium nuclei in regions corresponding to normal and abnormal tissue according to additional medical examination results. In some embodiments of the invention, the presence or absence of a disease is diagnosed based on a combination of the above comparisons.

In some embodiments of the invention, at least one additional medical examination is carried out, selected from magnetic resonance imaging on nuclei other than deuterium nuclei, ultrasound examination, computed tomography, radiography, palpation, biopsy, analysis of biological fluids for tumor markers, radionuclide diagnostics and/or visual observation. In some embodiments of the invention, additional medical examination is carried out before diagnosing a disease or pathological process using magnetic resonance imaging and/or deuterium magnetic resonance spectroscopy, as described above. In some other specific embodiments of the invention, additional medical examination is carried out after diagnostics of a disease or pathological process by magnetic resonance imaging and/or deuterium magnetic resonance spectroscopy, as described above.

In some specific embodiments of the invention, the presence or absence of a disease or pathological process is diagnosed based on a comparison of a deuterium tomogram of a subject undergoing an examination with an image obtained as a result of magnetic resonance imaging of a subject on the protium nuclei.

In some embodiments of the invention, a spatial distribution of a region with increased accumulation of the diagnostic drug on a deuterium tomogram, is used to make a conclusion about the spatial structure of a tumor.

In specific embodiments of the invention, the deuterium signal intensity on a deuterium tomogram and/or the NMR spectrum (spectra) in the area of increased accumulation of the diagnostic drug is used to make a conclusion about the malignancy or benignity of a tumor.

In some specific embodiments of the invention, the rate of change in the intensity of the deuterium signal on a deuterium tomogram and/or the NMR spectrum (spectra) after its administration is used to make a conclusion about the level of perfusion at different points of the scanned region.

Specific embodiments of the method for diagnosing a disease or pathological process in a subject related to the invention also include all embodiments of the invention in regard to the diagnostic drug described above.

In some embodiments of the method for diagnosing a disease or pathological process in a subject, the diagnostic drug to be administered comprises a deuterated derivative of sarcosine containing deuterium atoms in both the 2nd and 4th positions, or a pharmaceutically acceptable salt thereof; or a mixture of deuterated derivatives of sarcosine and/or their pharmaceutically acceptable salts, where there is at least one deuterated derivative, which contains deuterium atoms in the 2nd position, and at least one deuterated derivative, which contains deuterium atoms in the 4th position; at the same time, based on a comparison of the intensity of deuterium nuclei signals in the 2nd and 4th positions of the deuterated compound, a deuterium tomogram and/or NMR spectrum (spectra) in the target tissue is used to assess a local metabolic rate of sarcosine, which makes it possible to carry out a more accurate diagnostics, in particular, to evaluate the growth rate or malignancy of a tumor.

In some specific embodiments of the above-described embodiments of the invention, the deuterated sarcosine derivative is sarcosine-4,4,4-$d_3$, sarcosine-2,2-$d_2$ or sarcosine-2,2,4,4,4-$d_5$. In some specific embodiments of the above-described embodiments of the invention, the diagnostic drug comprises a mixture of at least two different compounds selected from a deuterated sarcosine derivative and/or a pharmaceutically acceptable salt of a deuterated sarcosine derivative. In some specific embodiments of the invention, the diagnostic drug comprises a mixture of at least two compounds selected from sarcosine-4,4,4-$d_3$, sarcosine-2,2-$d_2$, and sarcosine-2,2,4,4,4-$d_5$.

In some embodiments of the invention, the diagnostic drug is administered to a subject per os. In some other embodiments of the invention, the diagnostic drug is administered to a subject parenterally.

DEFINITIONS AND TERMS

Figure 1:
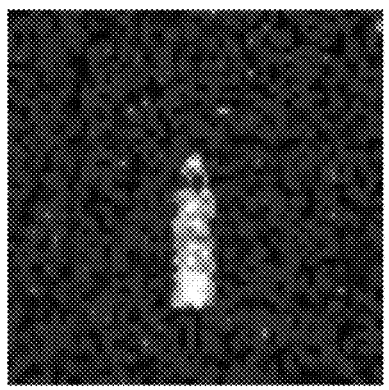
FIG. 1. a) deuterium tomogram (on the left) and $^2H$ spectrum (on the right) of the sample with sarcosine-4,4,4-$d_3$; b) deuterium tomogram (on the left) and $^2H$ spectrum (on the right) of the sample with sarcosine-2,2,4,4,4-$d_5$; c) deuterium tomogram (on the left) and $^2H$ spectrum (on the right) of the sample with a mixture of sarcosine-2,2-$d_2$ and sarcosine-4,4,4-$d_3$.
Figure 1:
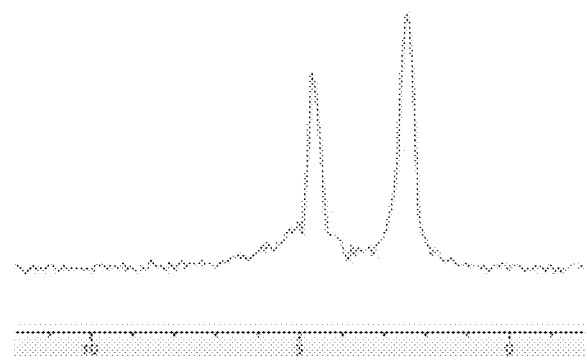
Figure 1:
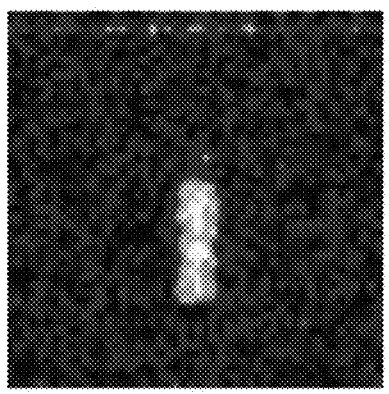
Figure 1:
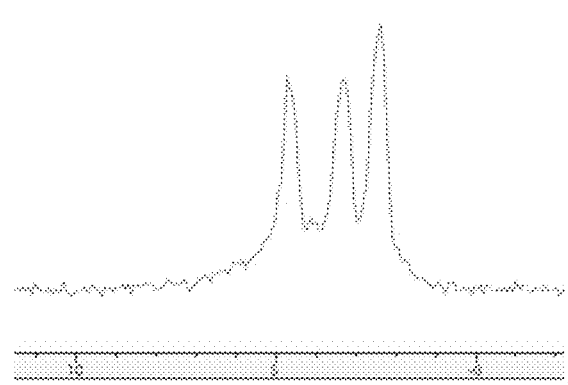
Figure 1:
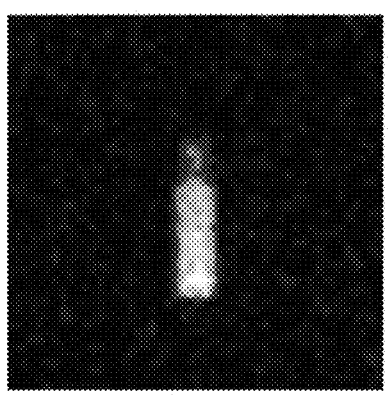
Figure 1:
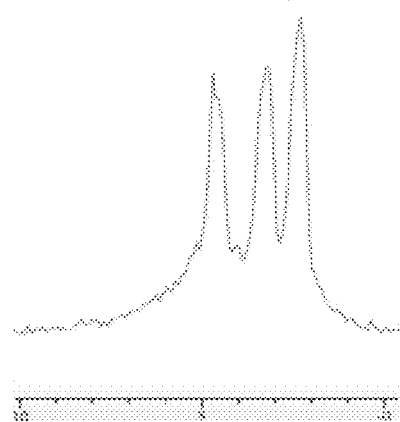

For a better understanding of the present invention, below are some of the terms used in the present description of the invention.

For the purposes of description of this invention, the terms "includes" and "including" are interpreted to mean "includes, among other things". These terms are not intended to be construed as "consists only of".

The term "subject" encompasses all mammalian species, preferably humans.

The term "deuterated derivative" in this document means a compound containing deuterium bound to carbon in an amount exceeding its natural content in at least one position. In specific embodiments of the invention, the deuterium content, at least in one position, exceeds 10%, in other specific embodiments—90%. "A mixture of at least two different deuterated derivatives" means a mixture of compounds containing deuterium in different positions, or containing different amounts of deuterium in the same position. The symbol "d" ("D") in this document denotes a hydrogen atom represented by the isotope $^2H$ in a proportion exceeding its natural content.

Deuterated sarcosine derivatives include sarcosine-4,4,4-$d_3$, sarcosine-2,2-$d_2$, sarcosine-2,2,4,4,4-$d_5$, as well as other derivatives such as sarcosine-2,4,4-$d_3$, sarcosine-2,2,4-$d_3$, sarcosine-2,4,4,4-$d_4$, sarcosine-4,4-$d_2$ but not limited to them (the numbering of atoms adopted herein is shown below).

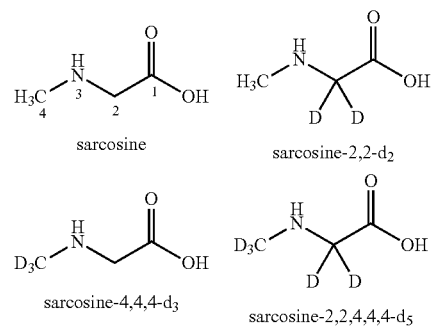

sarcosine sarcosine-2,2-$d_2$ sarcosine-4,4,4-$d_3$ sarcosine-2,2,4,4,4-$d_5$

The term "voxel" in this document refers to the minimum volume element of a scan area, which corresponds to a specific value of deuterium signal intensity or a specific local spectrum.

As used herein, the term "pharmaceutically acceptable salt" refers to those salts that are suitable for use in contact with human and animal tissues without undue toxicity, irritation, allergic reaction, etc., and meet a reasonable risk-benefit ratio. Pharmaceutically acceptable salts of amines, carboxylic acids, phosphonates, and other types of compounds are well known in the medicine. Salts can be prepared in situ during the isolation or purification of the compounds of the invention, and can also be prepared separately by reacting of a free acid or free base of the compound of the invention with a suitable base or acid, respectively. An example of pharmaceutically acceptable, non-toxic acid salts are salts of the amino group formed with inorganic acids such as hydrochloric, phosphoric, or organic acids such as acetic, oxalic, maleic, fumaric, tartaric, succinic, ascorbic, citric, butyric, lactic, gluconic acids, or obtained by other methods used in this field, for example, using ion exchange. Typical salts of alkali and alkaline earth metals contain sodium, potassium, calcium, magnesium and others. In addition, pharmaceutically acceptable salts may contain, if required, non-toxic ammonium, quaternary ammonium and amine cations obtained using counterions such as halides, hydroxides, carboxylates, sulfates, phosphates, and others.

The diagnostic drug of the invention may include one or more of any pharmaceutically acceptable excipients suitable for a particular dosage form, in particular, any carriers, diluents and/or fillers, such that can be administered to a patient's body together with a compound that constitutes the essence of this invention, and which do not destroy this compound, and are non-toxic when administered. Non-limiting specific examples of pharmaceutically acceptable excipients include sodium chloride, glucose, sweeteners, food flavors, and colorants, etc.

DETAILED DISCLOSURE OF THE INVENTION

The successful diagnostics of a disease using $^2$H MRI or MR spectroscopy is based on the ability of a particular deuterated compound to accumulate selectively in various tissues and, at the same time, to create a signal with an intensity sufficient from the point of view of the fundamental physical limitations of nuclear magnetic resonance methods (gyromagnetic ratio, relaxation parameters of deuterium nuclei). In this case, the intensity of the deuterium signal:
a) is proportional to the concentration of deuterium achieved in a tissue (depends on the dose, the kinetics of membrane transport, the concentrating ability of the tissue),
b) is proportional to the square root of the scan time (the time is limited by the rate of elimination and/or metabolism of the deuterated compound, as well as the need for a patient to stay immobile during the entire scanning procedure),
c) depends on the relaxation time T1 (determines the maximum averaging rate and, consequently, the intensity of the total signal received per unit of time; for different compounds it differs by several times: see. Biological Magnetic Resonance, Volume 11, In Vivo Spectroscopy. Berliner L. J., Reuben, J. (Eds.), Springer, 1992).

Each chemical compound has unique pharmacokinetic parameters (in particular, the concentration of the compound and the rate of its change in the blood, various organs and tissues). In this case, the pharmacokinetics in a non-obvious way depends on a dose used (in particular, an excess of the renal reabsorption capacity for a particular compound can lead to its accelerated excretion). At that, the dose is limited by the toxicity and solubility of this compound. Experiments carried out by the authors, as well as references to the prior art, show that freely diffusing deuterated compounds such as $D_2O$ do not show selective accumulation in various organs and tissues of a subject.

The authors have found that the deuterated derivatives of sarcosine, which are part of the diagnostic drug of the invention:
  are able to selectively accumulate in animal tissues at a concentration sufficient for visualization of various organs and tissues in vivo, including cancerous tumors, by $^2$H MRI or $^2$MR spectroscopy;
  possess pharmacokinetic properties that allow the use of non-toxic doses, while successfully registering $^2$H MRI and/or $^2$H NMR spectra;
  at concentrations sufficient for successful registration of $^2$H MRI and/or $^2$H NMR, they are characterized by rather slow excretion and metabolism, consistent with the time constraints of deuterium tomography and MR spectroscopy methods.

Although sarcosine is not a physiologically significant nutrient, the authors have found that it selectively accumulates in various organs and tissues of a subject at a concentration sufficient for imaging by means of MRI. In turn, this allows for effective diagnosis of diseases and pathological processes accompanied by a locally altered (increased or decreased) level of nutrients absorption by cells, including determining the presence and localization of an oncological disease, by means of deuterium magnetic resonance imaging. At the same time, our experiments have demonstrated that other amino acids, in particular, glycine-$d_2$, L-alanine-3,3,3-$d_3$ and L-phenylalanine β, β, 3,2,3,4,5,6-$d_7$ do not have suitable physical-chemical and biological properties and, therefore, cannot be used for the diagnosis of diseases by $^2$H MRI or MR spectroscopy.

A distinctive feature of deuterated derivatives of sarcosine is the opportunity to observe two signals of deuterium at once in MRI or MR spectroscopy when using a derivative containing deuterium atoms in both the 2nd and 4th positions, for example, sarcosine-2,2,4,4, 4-$d_5$ (FIG. 1b) or a mixture of sarcosines, where individual components contain deuterium atoms in the 2nd and/or in the 4th position (except the options which just include components containing deuterium atoms only in the 2 nd (or only in the 4th) position), for example a mixture of sarcosine-2,2-$d_2$ and sarcosine-2,2,4,4,4-$d_5$ or a mixture of sarcosine-4,4,4-$d_3$ and sarcosine-2,2-$d_2$. As distinct from the methods based on radioactive isotopes, this allows, in addition to the level of deuterated derivative accumulation, to obtain information on the metabolism of sarcosine based on the difference in the intensity of the drug deuterium signals. The intensity ratio of the NMR signals of deuterium atoms in the 2nd and 4th positions of sarcosine in this case reflects the differences between the target voxels of the scan region in the rate of oxidative demethylation (the first stage of metabolism) of sarcosine. It is known that sarcosine serves as a methyl group donor in the system of metabolism of one-carbon fragments (S. de Vogel et al. Int. J. Cancer, 2014, 134,1, 197-206). One-carbon fragments (mainly associated with tetrahydrofolate and S-adenosylmethionine) are used by the body, including for the synthesis of DNA necessary for cell proliferation. Thus, an increased local metabolic rate of sarcosine may indicate a locally increased proliferation rate, in particular, the growth of a tumor or its individual parts. The use of such additional diagnostic information about the metabolism of sarcosine makes the diagnostic method of the invention more reliable. The intensity ratio of NMR signals of deuterium atoms in the 2nd and 4th positions of sarcosine can be measured both once per scan and several times. A reduced signal ratio at the 2nd position to signal at the 4th position compared to the intact deuterated derivative is indicative of demethylation. Thus, the lower the ratio of these signals in a given voxel, the faster is demethylation of sarcosine in it.

The weight ratio of two different deuterated derivatives of sarcosine included in one diagnostic drug can be from 1:1 to 1:10, in the preferred embodiments, from 1:1 to 1:3, but is not limited to them.

It is known from the prior art that metabolism of deuterated sarcosine differs from that of non-deuterated sarcosine due to the kinetic isotope effect of the oxidation reaction of the N-methyl group (R. H. Abeles, W. R. Frisell, C. G. Mackenzie; J. Biol. Chem. 1960, 235, 3, 853-856). This makes it impossible to directly extrapolate the results obtained with ultra-low doses of radioactively labeled derivatives of sarcosine to deuterated derivatives of sarcosine of the invention, used in doses of more than 10 mg/kg, due to the fundamental limitations of the method of deuterium MRI.

It is known from the prior art that different amino acids have different kinetics of accumulation in animal and human cells, and also differ dozens of times in the concentration gradient achieved in the equilibrium state [Johnstone, R. M., Scholefield, P. G., Adv. Cancer Res. 1965, 9, 143-226]. The behavior of amino acids in vivo is further complicated by homeostasis and directed transport at the level of the whole body. In particular, it is known that excess alanine released by the muscles is actively absorbed by the liver; at a physiological concentration, glutamine is actively absorbed by several types of cancerous tumors. Since deuterium tomography or spectroscopy involves the administration of doses several times higher than physiological, and different organs and tissues are characterized by different accumulation kinetics and capacities for various amino acids, it is not possible to predict the presence of selective accumulation of a specific amino acid without a direct experiment.

An important property of the deuterated component (sarcosine) of the diagnostic drug of the invention is sufficient resistance to metabolic exchange of deuterium for protium in vivo. This exchange lowers the concentration of the deuterium label, while simultaneously increasing the background signal of heavy water (DOH), which is evenly distributed throughout the body due to rapid diffusion. This process leads to a decrease in the contrast of the image, and also prevents quantitive evaluation of deuterated component concentration by comparison with the intensity of natural DOH signal. Our studies have shown that some deuterated natural amino acids, in particular glycine-2,2-$d_2$ and L-alanine-3,3,3-$d_3$, cannot be used to obtain diagnostically significant images related to the invention, since they lose deuterium in vivovery quickly.

Due to low deuterium content in the body (0.015% hydrogen atoms), the background signals in $^2$H MRI are several orders of magnitude lower than in $^1$H MRI. Thus, even at a low concentration of the diagnostic drug, its signal is not superimposed on the signals of natural background components. The development of similar methods using non-deuterated diagnostic drugs based on $^1$H MRI is difficult due to the existence of a large number of background signals of natural low-molecular-weight compounds with an intensity comparable to the maximum achievable signal intensity of a non-deuterated diagnostic drug.

The method of the invention makes it possible to diagnose, in particular, the presence or absence of an oncological disease, accompanied by the formation of solid tumors (both primary and metastatic) and/or metastases in the lymph nodes. Oncological diseases that can be diagnosed with deuterated diagnostic drugs include: breast cancer, lung cancer, prostate cancer, melanoma, brain cancer (including metastases from other tumors), kidney cancer, colon cancer, pancreatic cancer, ovarian cancer, uterine cancer, non-Hodgkin's lymphoma, liver cancer, sarcoma, but not limited to them. In addition to oncological diseases, the method of the invention can be used in the diagnosis of other diseases characterized by high metabolic activity or cell proliferation: for example, in case of transplanted organs and cells rejection, in autoimmune, inflammatory or infectious diseases, in liver damage accompanied by active regeneration. It is also possible to diagnose diseases that develop as a result of blood supply disturbance (ischemia) of various organs, for example, heart, brain, kidneys. Blood supply disturbance leads to a decrease in the absorption rate and the achieved level of amino acids accumulation in these organs, including sarcosine, observed by using $^2$H MRI or MR spectroscopy. The method of the invention is based on the use of the deuterated diagnostic drug and registration of tomograms and/or NMR spectra at the deuterium frequency.

It is known that $^1$H MRI by itself in many cases has insufficient diagnostic accuracy. The same applies to the MRI methods based on measurement of perfusion parameters (e.g., dynamic contrast-enhanced MRI). In contrast to perfusion methods, the diagnostic method of the invention provides data on the rate of membrane transport and the level of sarcosine accumulation in cells, typical for PET or SPECT, and not available in traditional methods of $^1$H MRI implementing. Thus, the method of the invention provides more accurate diagnostic information. In particular, in case of an oncological disease, the method of the invention makes it possible to assess the metabolic activity of a a target tissue, and, as a consequence, to conclude that a tumor is malignant or benign, and to assess its aggressivity. The signal of the diagnostic drug of the invention can be observed for at least 3 hours (see FIG. 2). The rate of change in the signal intensity in a cancer tumor and various internal organs (liver, spleen, pancreas, kidneys) during repeated scanning for up to 3 hours reflects the level of perfusion and metabolic activity of these tissues and organs, which can be used to make a more accurate diagnosis based on deuterium tomography and/or MR spectroscopy.

In specific cases of the embodiment, the spatial distribution of the deuterium signal of the diagnostic drug is used to make a conclusion about the spatial structure of a tumor.

In other specific embodiments of the invention, the intensity of the deuterium signal in a region with an increased content of the diagnostic drug is used to make a conclusion about the degree of malignancy/aggressivity of a tumor. Malignant tumors are characterized by a more active metabolism and increased activity of membrane transport. Thus, in tumors with a higher grade of malignancy, the signal intensity of deuterium will be higher.

In other specific embodiments of the invention, the perfusion in a target area is assessed by the rate of change in the deuterium signal intensity of the diagnostic drug. In regions with a high degree of perfusion, the rate of change in the deuterium signal with time (from the start of accumulation in a tumor tissue to complete elimination) is higher.

The diagnostic drug of the invention is administered in an amount effective for the diagnosis. An effective amount in this case means that amount of a compound (deuterated derivative of sarcosine and/or a pharmaceutically acceptable salt thereof) administered or delivered to a patient when the desired effect is most likely to occur—the possibility of carrying out the diagnostic method of the invention by magnetic resonance imaging and/or deuterium magnetic resonance spectroscopy. Due to the fundamental limitations of the deuterium MRI method, the amount of deuterated sarcosine derivative and/or its pharmaceutically acceptable salt cannot be ultra-low and is used in an amount of several mg per kg of body weight, in doses exceeding 10 mg/kg, for example 0.1-1.5 g/kg. In particular, when calculating the dose of the drugs for mammals of different species, it is usually not weight that is used, but the surface area of a body, which is nonlinearly dependent on weight. The exact amount required may vary from subject to subject, depending on a mammal species, age, body weight and general condition of a patient, the severity of a disease, and the method of the drug administration.

Figure 2:
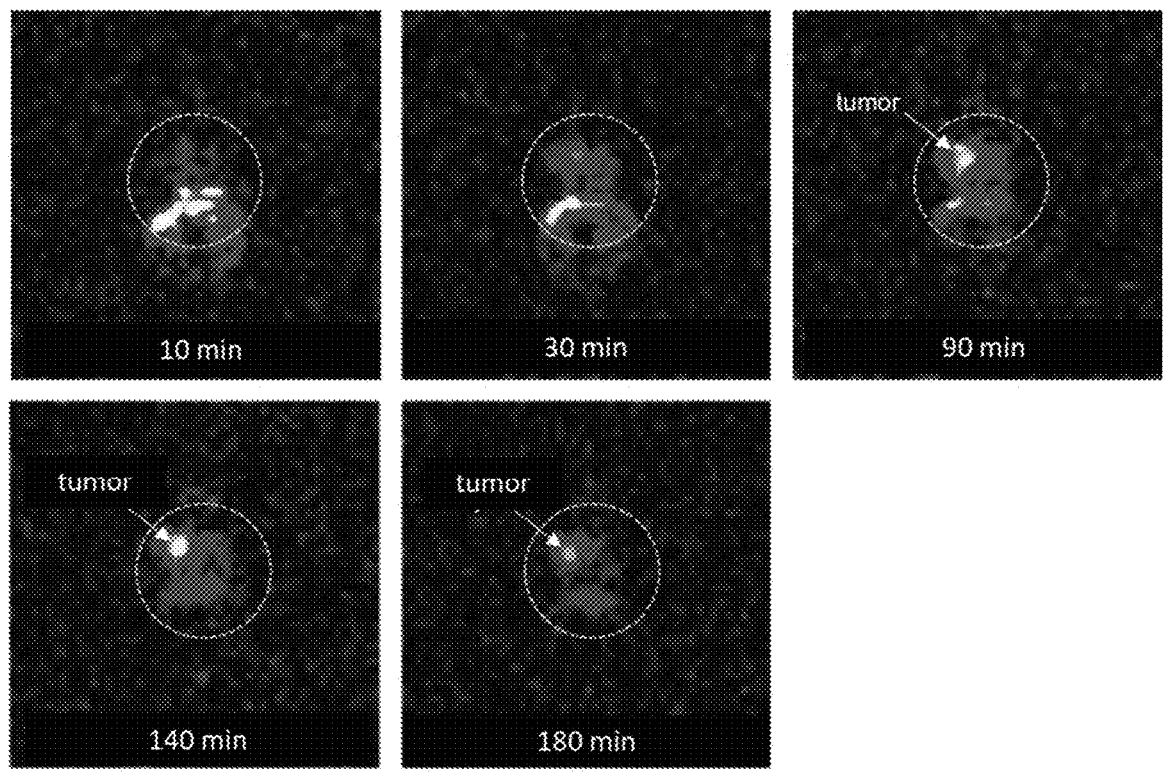
FIG. 2. Tomograms of the mouse No. 1 with breast carcinoma 4T1 after administration of 30 mg of sarcosine-4,4,4-$d_3$: a) $^2H$ tomograms obtained at different time points after administration; b) $^2H$ tomogram (on the left), overlay of $^2H$ and $^1H$ tomograms (in the center), $^1H$ tomogram (on the right).
Figure 2:
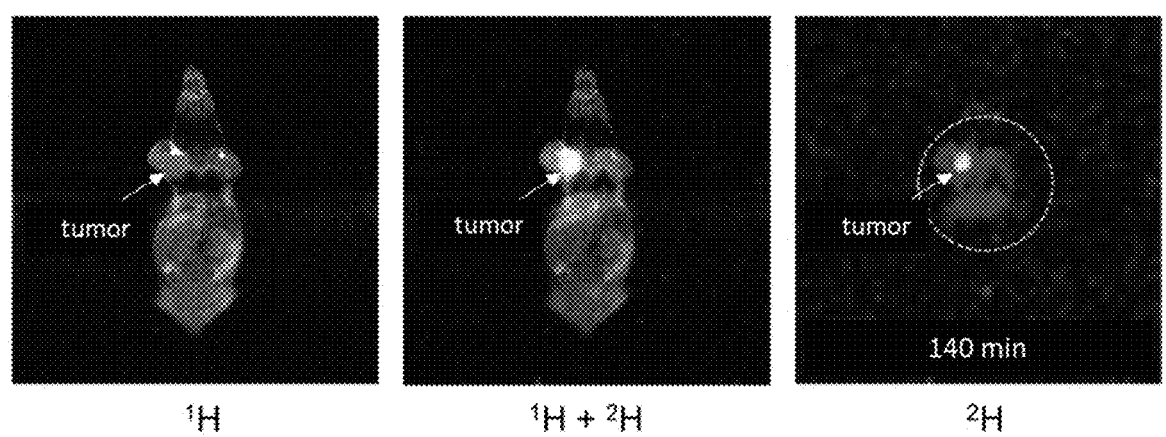

It is also known from the prior art that the half-life of the same compound can differ from one species to another (usually the half-life is longer in larger species), and therefore the optimal time between drug administration and scanning can differ significantly for different mammals. The optimal time between drug administration and scanning depends on the nature of a disease and the area of a subject's body being examined. As seen in FIG. 2, the subject's internal organs (liver, pancreas, spleen, etc.) appear on the deuterium tomogram before accumulation of sarcosine in the tumor reaches a maximum.

The diagnostic drug of the invention can be administered to a patient by any route of administration that is effective for the diagnosis, for example, it can be administered per os, parenterally, locally, etc.

Membrane transport of sarcosine is carried out by the same transporters as the transport of glycine and proline (F. H. Glorieux et al. J. Clin. Investigation, 1971, 50, 2313-2322). Glycine and proline inhibit the transport of sarcosine in proportion to their concentration and are characterized by a biodistribution that is different from that of sarcosine. Therefore, the administration of glycine and/or proline simultaneously with the drug of the invention or in the composition of the drug of the invention is capable of altering the levels of sarcosine accumulation in various organs and tissues of a subject. Such a change can enhance the contrast of deuterium imaging if the scanned organs and tissues of a subject accumulate sarcosine, glycine and/or proline to varying degrees.

Since membrane transport of sarcosine is carried out by several transporters with different affinities for different amino acids, the administration of amino acids using the same transporters as sarcosine, in particular glycine and proline, together with a deuterated derivative of sarcosine, makes it possible to inhibit the transport of sarcosine by individual transporters and, thus, selectively visualize the accumulation carried out by other transporters. The use of inhibitors, such as glycine and/or proline, can improve the contrast of the diagnostic image without changing the structure of the deuterated sarcosine derivative. Improvement of the contrast of diagnostic images due to the selective use of certain types of transporters during the transition from 2-deoxy-2- [$^{18}$F] fluoroglucose to methyl 4-deoxy-4- [$^{18}$F] fluoroglucoside has been previously demonstrated (V. Kepe et al. J. Neurooncol., 2018, 138, 5, 557-569), but, in contrast to this work, the method of the invention allows to change the selectivity of transport without changing the chemical structure of an active substance.

The oxidative demethylation of sarcosine is inhibited by several compounds such as acetate and methoxyacetate (W.R. Frisell, C. G. Mackenzie, J. Biol. Chem. 1955, 217, 1, 275-285). Administration of an acetate or other pharmaceutically acceptable inhibitor of sarcosine demethylation to a subject simultaneously with or as part of the diagnostic drug slows down the oxidation of the deuterated sarcosine derivative and thus increases the signal intensity of the deuterated derivative and/or the duration of its availability in a concentration sufficient to record deuterium MRI or spectra.

In one of embodiments of the invention, the diagnostic process includes MRI and is carried out as follows:

a) In some embodiments of the invention, protium ('H) nucleus MRI is carried out. Registration of $^1$H MRI allows, firstly, to carry out anatomical landmarks of the deuterium signal, and secondly, to identify regions with suspected pathology, in particular, a malignant neoplasm (in other embodiments, the region of 2″ MRI can be determined in other ways, in particular, by means of ultrasound, computed tomography, radiography, palpation, biopsy, analysis of biological fluids for tumor markers, radionuclide diagnostics and/or visual observation);

b) the diagnostic drug is administered;

c) after a time, sufficient for the accumulation of the diagnostic drug in a target tissue of a subject, the tomogram is recorded at the frequency of the precession of the diagnostic drug deuterium nuclei;

d) the obtained deuterium tomograms are analyzed in order to find regions with abnormally high or low intensity and, therefore, corresponding to the selective accumulation of the diagnostic drug. In particular, it is possible to compare tomograms obtained on $^1$H and $^2$H: if the abnormal regions on $^1$H and $^2$H coincide, it can be said that there is a greater likelihood of the pathology.

In another embodiment of the invention, the diagnostic process includes conducting deuterium MR spectroscopy and is carried out as follows:

a) $^1$H MRI is carried out, then the regions with suspected pathology, in particular, malignant neoplasm are identified (in other embodiments of the invention, the determination of the $^2$H MRI region can be carried out by other methods, in particular, by means of ultrasound examination, computed tomography, radiography, palpation, biopsy, analysis of biological fluids for tumor markers, radionuclide diagnostics and/or visual observation);

b) the diagnostic drug is administered;

c) after a time, sufficient for the accumulation of the diagnostic drug in a target tissue of a subject in voxels corresponding to a region with suspected pathology (for example, according to the results of $_1$H MRI), the deuterium spectrum is recorded (in particular, using the methods of local spectroscopy); optionally, the spectrum is registered in adjacent voxels to compare the signal intensity;

d) the signal intensity in voxels corresponding to the area with suspected pathology is compared, in particular, with: (i) typical values for a given organ or tissue (which should be determined in advance in healthy subjects) and/or (ii) intensity in adjacent voxels corresponding to the same organ or tissue and free from abnormalities on $^1$H MRI. An increased or decreased signal intensity suggests a selective accumulation of the diagnostic drug and, as a consequence, the presence of pathology, in particular, a malignant neoplasm.

The order of steps "a), b), c)" in both of the above embodiments of the invention can be changed to "b), a), c)" or "b), c), a)". It is also possible to register signals $^1$H and $^2$H in parallel (i.e., simultaneous carrying out of stages "a)" and "c)").

In specific embodiments of the invention after identifying a region with suspected malignant formation, individual voxels are selected that lie both within and outside the suspicious region (in particular, a series of adjacent voxels lying on the same line crossing the border of a suspicious area can be selected). Registration of the integral signal of $^2$H or local $^2$H spectra in the selected voxels with subsequent comparison of their intensity makes it possible to quickly and with greater sensitivity to detect the regions where the diagnostic drug is accumulated.

MRI images and MR spectra can be obtained on any MRI scanner fitted with equipment for recording the deuterium signal.

The examinations carried out by the authors of the invention indicate a good tolerance of the diagnostic drug by animals, the absence of visible side effects when used in the indicated doses on any MRI scanner fitted with equipment for registering a signal of deuterium. It is known from the prior art that sarcosine is safe when administered in high doses ($LD_{50}$>5 g/kg). Considering the effective catabolism of a natural sarcosine with the concomitant release of deuterium in the form of DOH (non-toxic in very high doses, up to the replacement of 10-30% of water in the body, and is also present in the body water at a concentration of about $1 \times 10^{-2}$ mol/l), we do not expect side effects associated with the administration of multiple deuterium atoms.

The method of the invention is carried out without the harmful effects of ionizing radiation (typical, for example, for CT, PET, SPECT), which in turn increases the safety of examinations, makes it possible to conduct more frequent repeated studies, in particular, makes the method attractive for pediatrics.

The diagnostic method of the invention can be used, in particular, for the early diagnosis of malignant tumors of various localization, metastatic lesions, assessment of a tumor response to treatment and conclusions about the effectiveness of the therapy, to clarify the diagnosis based on the results of $^1$H MRI and/or other diagnostic methods.

The method of the invention expands the existing possibilities of non-invasive diagnostics, and allows for effective diagnosis of oncological diseases.

The pharmaceutically acceptable salts of deuterated sarcosine derivatives have all the properties required for their use in the diagnostic drug of the invention.

Implementation of the Invention

The possibility of objective manifestation of the technical result when using the invention is confirmed by reliable data given in the examples containing experimental data obtained in the process of conducting research according to the methods applied in this field. The essence of the invention is illustrated by the figures.

It should be understood that these and all examples given in the application materials are not limiting and are given only to illustrate the present invention.

The examples given in this document serve to illustrate the principle of operation of the developed method and do not limit the range of doses used, as well as the range of time between the administration of the diagnostic drug and the registration of the deuterium signal, since, depending on the sensitivity and other parameters of the equipment used, a diagnosed disease and a nature of a subject (human or laboratory animal), the required doses and the time required for drug accumulation may differ. In particular, it is known from the prior art that the half-life of the same compound can vary between animal species, and that when changing from one animal to another or to humans, doses tend to scale in proportion to body surface area rather than a body weight. In addition, the above parameters for recording spectra and tomograms, including the signal accumulation time, are part of specific embodiments of the invention and may vary depending on the equipment used and specific diagnostic tasks.

Synthesis of N— ($CD_3$) -glycine (sarcosine-4,4,4-$D_3$).

N-tosylglycine was obtained according to the method described in literature (A. Cohen et al. J. Labelled Compounds and Radiopharmaceuticals, 1986, 24, 5, 587-597).

3.29 g of tosylglycine (0.014 mol) was dissolved in 17.2 ml of 3M NaOH. The resulting solution was placed in a glass autoclave and cooled in an ice bath. To a cold solution of tosylglycine in aqueous alkali, 3.25 g (0.022 mol) of $CD_3I$ was added with stirring. The reaction mixture was placed in a water bath preheated to 85° C. and vigorously mixed at a given temperature for 8 h. The mixture was then cooled to room temperature and left in the refrigerator overnight. The reaction mixture was cooled in an ice bath and 4 ml of cold concentrated HCl was added with stirring. The resulting suspension was stirred for 1 h in an ice bath, then the light yellow precipitate was filtered off. Yield of N-tosylsarcosine-4,4-$d_3$: 3.15 g (92%).

$^1$H NMR spectrum (600 MHz, DMSO-$d_6$, ppm): δ=7.67 (2H, d, $^3$J=8.2 Hz, 2,6-Ar), 7.71 (2H, d, $^3$J=8.2 Hz, 3,4 Ar), 3.84 (2H, s, $CH_2$), 2.39 (3H, s, $ArCH_3$).

$T_m$=149-151° C.

A solution of tosylsarcosine-$d_3$ 2.8 g (0.011 mol) in 12 ml of concentrated HCl was vigorously mixed at 100° C. for 14 h. Thereafter, the mixture was cooled to room temperature and diluted with water. The resulting solution was concentrated on a rotary evaporator (38° C. water bath), re-diluted with water, and concentrated again to remove hydrochloric acid. The product was isolated from the reaction mixture, consisting of the product itself, residual hydrochloric acid and TsOH using ion exchange chromatography as follows: the mixture in the form of a dilute aqueous solution (200 ml) was passed at a rate of 0.1 volumes per minute through a column containing 46 ml (88 meq) of Dowex 50 resin. The column was washed with water until a neutral eluate of 300 ml emerged. The product was eluted with 250 ml of 1M $NH_4OH$ solution and dried on a rotary evaporator. Yield of sarcosine-4,4,4-$d_3$: 0.86 g (85%).

$^1$H NMR spectrum (600 MHz, $D_2O$, ppm): δ=3.59 (s, $CH_2$).

$T_m$=202-204° C.

Synthesis of sarcosine-2,2-$D_2$.

Tosylglycine 0.47 g (0.002 mol) was dissolved in a solution of sodium alkali in $D_2O$ prepared from 3.5 ml of $D_2O$ and 0.29 g (0.007 mol) of NaOH. The resulting solution was placed in a glass autoclave and cooled in an ice bath. To a cold solution of tosylglycine in aqueous alkali, 0.46 g (0.003 mol) of $CH_3I$ was added with magnetic stirring. The reaction mixture was placed in a water bath preheated to 85° C. and vigorously mixed at a given temperature for 8 h. The mixture was then cooled to room temperature and left in the refrigerator overnight. The reaction mixture was cooled in an ice bath, and 0.7 ml of cold concentrated HCl was added while stirring. The resulting suspension was stirred for 1 h in an ice bath, then the light yellow precipitate was filtered off. The product does not need to be purified for further reactions. Yield of N-tosylsarcosine-2,2-$d_2$: 0.44 g (90%).

$^1$H NMR spectrum (600 MHz, DMSO-$d_6$, ppm): δ=7.67 (2H, d, $^3$J=8.2 Hz, 2,6-Ar), 7.71 (2H, d, $^3$J=8.2 Hz, 3,4 Ar), 2.74 (3H, s, NMe), 2.39 (3H, s, ArCH$_3$).

$T_m$=149-151° C.

The hydrolysis was carried out similar to the procedure described above for sarcosine-4,4-$d_3$. Yiled of sarcosine-2,2-$D_2$: 84%.

$^1$H NMR spectrum (600 MHz, $D_2O$, ppm): δ=2.68 (s, CH$_3$).

$T_m$=200-203° C.

Synthesis of sarcosine-2,2,4,4,4-$d_5$.

N-tosylsarcosine-2,2,4,4,4-$d_5$ was obtained similarly to the previous example, but using $CD_3I$ instead of $CH_3I$. Yield: 88%.

$^1$H NMR spectrum (600 MHz, DMSO-ds, ppm): δ=7.67 (2H, d, $^3$J=8.2 Hz, 2,6-Ar), 7.71 (2H, d, $^3$J=8.2 Hz, 3,4 Ar), 2.39 (3H, s, ArCH$_3$).

$T_m$=150-152° C.

The hydrolysis was carried out similar to the procedure described above for sarcosine-4,4-$d_3$. Yield of sarcosine-2,2,4,4,4-$D_5$: 85% $^1$H NMR spectrum (600 MHz, $D_2O$, ppm): The spectrum contains only signals of residual protons of the solvent.

$T_m$=200-203° C.

In the examples below, a Bruker BioSpec BC70/30 USR tomograph with a constant field of 7.05 T was used, equipped with a cavity resonator tuned to $^1$H (transmit/receive) and $^2$H (transmit), and a surface receive coil with a diameter of 5 cm.

The deuterium tomogram was recorded using FLASH (Fast low angle shot) pulse sequence. The excitation frequency was determined from the $^2$H NMR spectrum and was on the instrument used: sfo1≈46.17452 MHz, rectangular excitation pulse 2560 Hz wide and 11.2 dB power, deflection angle FA=30°, repetition time TR=11.8 ms, echo time TE=4.07 ms, scan region10 cm×10 cm, scan matrix 50×50, slice thickness 3 cm, bandwidth 12500 Hz, total scan time 9 minutes 34 seconds (1024 accumulations).

EXAMPLE 1

Registration of Deuterium Tomogram and $^2$H NMR Spectrum of a Sample Containing a Dilute Solution of Deuterated Sarcosine To demonstrate the fundamental possibility of registering a deuterium tomogram of a deuterated sarcosine diluted solution, the following experiment was carried out.

Glass vial containing 5 ml of a solution of sarcosine-4,4,4-$d_3$ (5 mg) or sarcosine-2,2,4,4,4-$d_5$ (5 mg) or a mixture of sarcosine-4,4,4-$d_3$ (5 mg) and sarcosine-2,2-$d_2$ (5 mg) in distilled water, was placed in the center of the tomograph magnet. A surface coil 5 cm in diameter was positioned directly above the vial.

FIG. 1a shows the deuterium tomogram (on the left) and a $^2$H spectrum (on the right) of the sample with sarcosine-4,4,4-$d_3$. FIG. 1b shows a deuterium tomogram (on the left) and a $^2$H spectrum (on the right) of the sample with sarcosine-2,2,4,4,4-$d_5$. FIG. 1c shows a deuterium tomogram (on the left) and a $^2$H spectrum (on the right) of the sample with a mixture of sarcosine-2,2-$d_2$ and sarcosine-4,4,4-$d_3$.

EXAMPLE 2

Use of Deuterium Tomography to Visualize Mouse 4T1 Breast Carcinoma In Vivo Using the Diagnostic Drug Containing Sarcosine-4,4,4-$d_3$ In this example, experiments were performed on Balb/c mice grafted with 4T1 breast carcinoma (injection of 5×10$^5$ cells/60 μl under the left forepaw 12 days before the experiment). An animal weighing 20 g was injected intraperitoneally with a solution of 30 mg sarcosine-4,4,4-$d_3$ in 0.5 ml of water. In 10 minutes after the injection, the animal was immobilized with isoflurane and placed on a heated bed in a tomograph. The surface $^2$H receiving coil was positioned over the anterior part of the animal's body from the dorsal side, as indicated in FIG. 2 by the dotted line.

FIG. 2 shows that the start of the deuterated sarcosine derivative accumulation in the tumor tissue is observed within a few minutes after administration, over time, the deuterated sarcosine derivative accumulates in the tumor tissue, and the maximum intensity of the deuterium signal is observed approximately 90-140 minutes after the drug administration. As can be seen from the data given, the deuterium signal persists for several tens of minutes; thus, sarcosine-4,4,4-$d_3$ has favorable pharmacokinetics for practical use in $^2$H MRI and MR spectroscopy.

As follows from the above results, the diagnostic drug based on a deuterated sarcosine derivative is capable of accumulating in pathological (tumor) tissue at a concentration sufficient to register an informative deuterium tomogram or $^2$H-NMR spectrum in vivo and, therefore, can be used for non-invasive diagnosis of diseases, including oncological, by $^2$H MRI and/or MR spectroscopy.

EXAMPLE 3

The use of Deuterium Tomography for Visualization of Mouse 4T1 Breast Carcinoma In Vivo Using the Diagnostic Drug Containing L-alanine-3,3,3-$d_3$ and L-phenylalanine-β, β, 43, 2,3,4,5,6-$d_7$.

In this example, experiments were performed on Balb/c mice grafted with 4T1 breast carcinoma (injection of 5×10$^5$ cells/60 μl under the left forepaw 12 days before the experiment).

An animal weighing 20 g was injected intraperitoneally with a solution:

a) 30 mg of L-alanine-3,3,3-$d_3$ in 0.5 ml of water; or b) 10 mg of L-phenylalanine-β, β, 2,3,4,5,6-d7 in 1.0 ml of water (a lower dose of phenylalanine equivalent to deuterium is due to the low solubility of phenylalanine and, as a consequence, the impossibility of introducing a larger volume of the diagnostic drug without harm for the health of a subject).

In 10 minutes after the injection, the animal was immobilized with isoflurane and placed on a heated bed in a tomograph. The surface $^2$H receiving coil was positioned over the anterior part of the animal's body from the dorsal side, as indicated in FIG. 3 by the dotted line.

Figure 3:
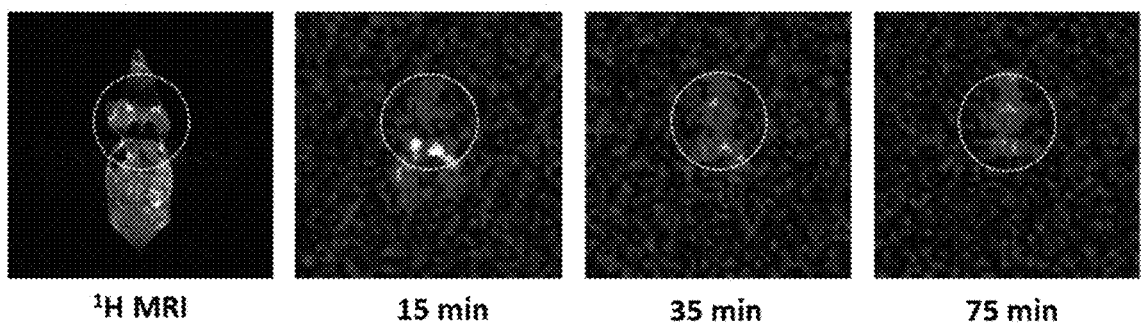
FIG. 3. Tomograms of the mouse with 4T1 breast carcinoma after administration of: a) 30 mg of L-alanine-3,3,3-$d_3$; b) 10 mg of L-phenylalanine-β, β, 2,3,4,5,6-$d_7$.
Figure 3:
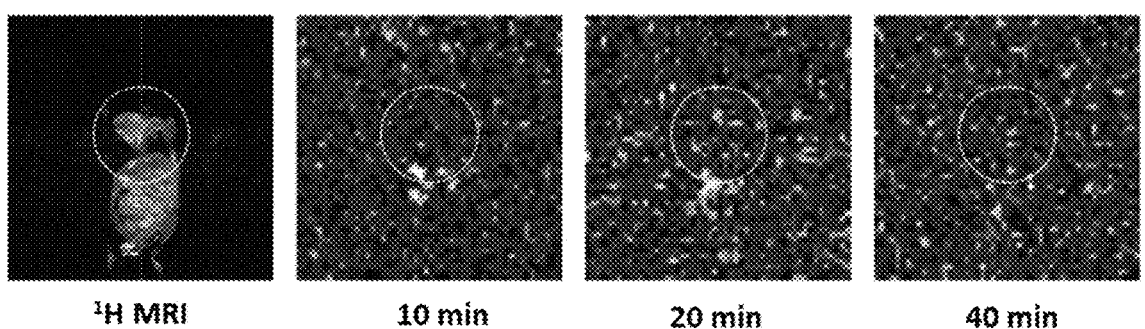

FIG. 3 shows that deuterated derivatives of alanine and phenylalanine do not accumulate in tumor tissue and do not show accumulation selectivity in various organs. This indicates that deuterated derivatives of alanine and phenylanine cannot be used to diagnose oncological diseases by $^2$H MRI or MR spectroscopy.

Although the invention has been described with reference to the disclosed embodiments, it should be apparent to the subject matter experts that the specific experiments described in details are provided for the purpose of illustrating the present invention only and should not be construed as in any way limiting the scope of the invention. It should be understood that various modifications are possible without departing from the spirit of the present invention.

The invention claimed is:

1. A method of diagnosing an oncological disease in a subject, the method comprising:
   (a) a diagnostic drug comprising at least one compound selected from a deuterated derivative of sarcosine and/or a pharmaceutically acceptable salt of a deuterated derivative of sarcosine is administered to the subject;
   (b) deuterium magnetic resonance imaging and/or deuterium magnetic resonance spectroscopy is carried out after the administration of the diagnostic drug in a time sufficient for its accumulation in a target tissue, to obtain, respectively, a tomogram and/or NMR spectrum (spectra); and
   (c) the presence or absence of an oncological disease is diagnosed based on the observed signal intensity of deuterium nuclei, reflecting the level of accumulation of the diagnostic drug.

2. The method according to claim 1, wherein the oncological disease is a cancer tumor.

3. The method according to claim 1, wherein at least one additional medical examination is performed, selected from magnetic resonance imaging on nuclei other than deuterium nuclei, ultrasound examination, computed tomography, radiography, palpation, biopsy, analysis of biological material of the subject for tumor markers, radionuclide diagnostics and/or visual observation.

4. The method according to claim 1, wherein the presence or absence of an oncological disease is diagnosed based on comparing the signal intensity of deuterium nuclei in the subject under examination with the typical signal intensity observed in healthy subjects in a corresponding tissue or corresponding organ.

5. The method according to claim 1, wherein the presence or absence of an oncological disease is diagnosed based on a comparison of the deuterium signal intensity in regions corresponding to normal and abnormal tissue according to additional medical examination data.

6. The method according to claim 1, wherein the diagnostic drug includes:
   a deuterated derivative of sarcosine containing deuterium atoms in both the 2nd and 4th positions, or a pharmaceutically acceptable salt thereof; or
   a mixture of deuterated derivatives of sarcosine and/or pharmaceutically acceptable salts thereof, in which at least one deuterated derivative is present, which contains deuterium atoms in the 2nd position, and at least one deuterated derivative, which contains deuterium atoms in the 4th position,
   and wherein the level of metabolic activity and/or proliferation of cells of a target tissue is additionally assessed based on a comparison of the intensity of deuterium signals in the 2nd and in the 4th position.

7. The method according to claim 3, wherein the presence or absence of an oncological disease is diagnosed based on the comparison of a currently obtained deuterium magnetic resonance imaging and/or deuterium magnetic resonance spectroscopy of the subject under examination with an image obtained as a result of protium magnetic resonance imaging of the subject.

8. The method according to claim 2, wherein the spatial distribution of a region with increased accumulation of the diagnostic drug is used to make a conclusion about the structure of a tumor.

9. The method according to claim 2, wherein the intensity of the deuterium signal in a region of increased accumulation of the diagnostic drug is used to make a conclusion about the malignancy or benignity of a tumor.

10. The method according to claim 1, wherein the rate of deuterium signal intensity change after injection is used to make a conclusion about the level of perfusion in different parts of a scanned region.

11. The method according to claim 1, wherein the diagnostic drug is administered to the subject per os.

12. The method according to claim 1, wherein the diagnostic drug is administered to the subject parenterally.

13. The method according to claim 1, wherein the magnetic resonance imaging and/or deuterium magnetic resonance spectroscopy is performed 10-180 minutes after the administration of the diagnostic drug.

14. The method according to claim 1, wherein the deuterated derivative of sarcosine is sarcosine-4,4,4-$d_3$, sarcosine-2,2-$d_2$, sarcosine-2,2,4,4,4-$d_5$.

15. The method according to claim 1, wherein the deuterated derivative of sarcosine is a mixture of at least two different compounds selected from a deuterated sarcosine derivative and/or a pharmaceutically acceptable salt of a deuterated derivative of sarcosine.

16. The method according to claim 1, wherein the deuterated derivative of a sarcosine and/or pharmaceutically acceptable salt of a deuterated derivative of sarcosine, along with deuterium atoms bonded to carbon atoms, contain deuterium atoms partially or completely replacing mobile hydrogen atoms bonded to oxygen atoms and/or nitrogen.

17. The method according to claim 1, wherein the oncological disease is a solid tumor or tumor metastases.

18. The method according to claim 1, wherein the oncological disease is a breast cancer.

* * * * *